(12) United States Patent
Chong

(10) Patent No.: US 11,806,221 B2
(45) Date of Patent: Nov. 7, 2023

(54) PROTECTIVE INSERT AND A GARMENT INCLUDING SUCH PROTECTIVE INSERT

(71) Applicant: Modibodi Australia Pty Ltd, Drummoyne (AU)

(72) Inventor: Kristy Chong, Gladesville (AU)

(73) Assignee: Modibodi Australia Pty Ltd, Drummoyne (AU)

( * ) Notice: Subject to any disclaimer, the term of this patent is extended or adjusted under 35 U.S.C. 154(b) by 565 days.

(21) Appl. No.: 16/639,074

(22) PCT Filed: Aug. 15, 2018

(86) PCT No.: PCT/AU2018/050865
§ 371 (c)(1),
(2) Date: Feb. 13, 2020

(87) PCT Pub. No.: WO2019/033163
PCT Pub. Date: Feb. 21, 2019

(65) Prior Publication Data
US 2020/0222256 A1 Jul. 16, 2020

(30) Foreign Application Priority Data
Aug. 17, 2017 (AU) .............................. 2017903309

(51) Int. Cl.
*A61F 13/49* (2006.01)
*A61F 13/84* (2006.01)
(Continued)

(52) U.S. Cl.
CPC ........ *A61F 13/8405* (2013.01); *A61F 13/476* (2013.01); *A41B 9/04* (2013.01);
(Continued)

(58) Field of Classification Search
CPC ...... A61F 13/472; A61F 13/476; A61F 13/72; A61F 2013/15121; A61F 2013/15195;
(Continued)

(56) References Cited

U.S. PATENT DOCUMENTS 4,352,356 A * 10/1982 Tong ..................... A61F 13/74
604/397
10,231,885 B2 * 3/2019 Hovey .............. A61F 13/49006
(Continued)

FOREIGN PATENT DOCUMENTS

AU 2010229644 B2 10/2011
AU 2018317934 2/2020
(Continued)

OTHER PUBLICATIONS

International Search Report and Written Opinion for PCT/AU2018/050865, dated Oct. 18, 2018.
(Continued)

*Primary Examiner* — Catharine L Anderson
(74) *Attorney, Agent, or Firm* — Klarquist Sparkman LLP

(57) ABSTRACT

A protective insert (10) operatively attachable to an inner, body-facing layer of a garment. The protective insert generally comprises, a first, operatively inner layer (12) comprising a moisture-wicking, odour resistance, fluid absorbent fibre with or without a waterproof laminate-film; and a second, operatively outer layer (14) comprising a breathable, odour resistant, water repellent fibre to further prevent fluid passage through the garment; wherein the operatively inner layer faces the body of a user while the operatively outer layer faces away from the body of a user, in use.

26 Claims, 4 Drawing Sheets

(51) Int. Cl.
    *A61F 13/476* (2006.01)
    *A41B 9/04* (2006.01)
    *A41D 7/00* (2006.01)
    *A61F 13/472* (2006.01)
    *A41D 27/04* (2006.01)
    *A61F 13/15* (2006.01)
    *A61F 13/511* (2006.01)
    *A61F 13/514* (2006.01)

(52) U.S. Cl.
    CPC ............ *A41B 2400/34* (2013.01); *A41D 7/00* (2013.01); *A41D 27/04* (2013.01); *A61F 13/472* (2013.01); *A61F 2013/15121* (2013.01); *A61F 2013/51139* (2013.01); *A61F 2013/51441* (2013.01)

(58) Field of Classification Search
    CPC .. A61F 2013/51061; A61F 2013/51064; A61F 2013/51139; A61F 2013/51441
    See application file for complete search history.

(56) References Cited

U.S. PATENT DOCUMENTS

| | | | | |
|---|---|---|---|---|
| 2009/0299313 | A1* | 12/2009 | Knightingale | A61F 13/8405 604/385.03 |
| 2011/0087184 | A1 | 4/2011 | Wöhlke et al. | |
| 2012/0010582 | A1* | 1/2012 | Newnam | A61F 13/505 604/385.15 |
| 2014/0025027 | A1* | 1/2014 | Png | A61F 13/665 604/385.15 |
| 2014/0039432 | A1* | 2/2014 | Dunbar | A61F 13/66 604/394 |
| 2016/0184146 | A1* | 6/2016 | Tulk | A01N 37/06 604/385.15 |

FOREIGN PATENT DOCUMENTS

| | | |
|---|---|---|
| EP | 0627177 | 12/1994 |
| EP | 3668466 | 6/2020 |
| WO | WO2001/087215 A1 | 11/2001 |

OTHER PUBLICATIONS

Extended European Search Report for European Application No. 18846188.3, dated Mar. 12, 2021.

Examination report dated Aug. 26, 2022 issued by the Australian Patent Office on corresponding patent application AU 2018317934; 5 pages.

Spruch-Feiner, 'The Best Workout Leggings for Going Commando,' Dec. 9, 2016, (https://www.racked.com/2016/12/9/13887990/best-workout-leggings-no-underwear). Racked; 28 pages.

* cited by examiner

PROTECTIVE INSERT AND A GARMENT INCLUDING SUCH PROTECTIVE INSERT

CROSS REFERENCE TO RELATED APPLICATIONS

This is the U.S. National Stage of International Application No. PCT/AU2018/050865, filed Aug. 15, 2018, which was published in English under PCT Article 21(2), which in turn claims the benefit of Australian Application No. 2017903309, filed Aug. 17, 2017, which applications are incorporated herein in their entireties.

TECHNICAL FIELD

This invention relates to a protective insert for dance, active and swimwear, in general. More particularly, this invention relates to reusable protective dance, active and swimwear, and to a method of manufacturing reusable dance, active and swimwear including such a protective insert.

BACKGROUND ART

The following discussion of the background art is intended to facilitate an understanding of the present invention only. No acknowledgement or admission that any of the material referred to is or was part of the common general knowledge as at the priority date of the application is intended.

Women and men occasionally experience failure with their dance, active and swimwear due to leakage of bodily fluids or secretions past, or through, such garments. The Applicant is aware of conventional reusable dance, active and swimwear, which offers very little, to no, protection against moisture egress in the form of bodily fluids or secretions. Because regular dance, active and swimwear of which the Applicant is aware does not offer significant protection from leakage, it often results in embarrassing situations, or it means that users do not participate in swimming, dancing and exercise for fear of leakage.

Many women experience light bladder leaks (experienced by 30% of women with one child or more, and often a result of urge incontinence in young toilet training children), menstrual overflow (experienced by 50% of women during menstruation due to tampon or mooncup failure), heavier discharge (experienced regularly by many women) and breastmilk leakage (experienced by most breastfeeding mothers), and are hence forced to use disposable hygiene products with their active, dance and swimwear, or not participate at all. This is both uncomfortable and may reduce the likelihood that such persons may partake in dancing, exercise, swimming or aquatic activities.

It is an objective of this invention to address some of the issues of existing active, dance and swimwear products and to create garments that look, fit and feel like regular active wear, dance leotards and swimwear but offers increased protection against inadvertent leakage when compared to conventional garments of which the Applicant is aware.

SUMMARY OF INVENTION

The skilled addressee will appreciate that reference herein to a 'garment' includes reference to any form of dance, active and/or swimwear and any article of clothing useable for dancing, exercise and/or swimming or related physical activities.

According to one aspect of the invention, there is provided a protective insert operatively attachable to an inner, body-facing layer of a garment, the protective insert comprising:

a first, operatively inner layer comprising a moisture-wicking, odour resistant, fluid absorbent fibre with or without a waterproof laminate-film; and a second, operatively outer layer comprising a breathable, odour resistant, water repellent fibre to further prevent fluid passage through the garment;

wherein the operatively inner layer faces the body of a user while the operatively outer layer faces away from the body of a user, in use.

The fibre used in the first, operatively inner layer may be a natural fibre, derived from natural fibre, or may be a synthetic fibre like polyester or nylon, or a combination of natural and synthetic fibres.

The first, operatively inner layer fibre may be configured to be hydrophilic or contain a hydrophilic compound.

The fibre may be chosen to allow for the spreading and drying of 5-10 ml of moisture or bodily secretions in a rapid fashion (e.g. less than 5-10 minutes for drying each ml of moisture or bodily secretions per 10 cm×10 cm section of fabric).

The first, operatively inner layer fibre may be in the form of a synthetic fibre, typically in the form of polyester and typically in the form of a woven or knitted mesh fabric. The inner layer may contain bamboo or charcoal and may have an antimicrobial treatment like Silpure® applied and odour absorbing treatment like Zeomic® applied.

The first, operatively inner layer fibre may be in the form of a bamboo charcoal-containing fibre, typically contained in the form of a woven or knitted mesh fabric. The fabric may include bamboo charcoal-containing fibre and may include at least one synthetic fibre, typically in the form of polyester, associated with the bamboo charcoal, thereby forming a bamboo charcoal polyester fabric.

The fabric may be a mesh, generally in the form of a knitted fabric.

The fabric may be moisture-wicking or pre-treated to enhance the moisture-absorbing or moisture-wicking capabilities thereof.

The fabric may be selected to possess natural antimicrobial properties, like charcoal, and/or may also be treated with an antimicrobial and/or odour absorbing composition.

The antimicrobial composition may be an antibacterial, antiviral, or antifungal compound, or a combination of such compounds.

The antimicrobial composition may be in the form of silver ions or derivatives thereof. The antimicrobial composition may be complexed with other antimicrobial compositions or carriers. The antimicrobial composition may be commercially available antimicrobial compositions available under the trade name Silpure® or Ultrafresh®.

The odour absorbing composition may be in the form of Zeomic® and/or Sciessent® product range like Lava®, Agion® or Active® or other treatments that are renowned for ammonia and body odour absorption.

The first, operatively inner layer may be associated with a clear breathable waterproof laminate-film on the outer side for additional waterproof effect.

The first, operatively inner layer fibre may be included in a weight in a range of 100 gsm to 300 gsm, preferably between 150 gsm and 250 gsm, most preferably 200 gsm.

The first, operatively inner layer may have a thickness of between 0.5 mm and 2.5 mm, preferably between 0.8 mm and 2 mm, most preferably less than 1 mm.

The operatively outer (i.e. swim, dance or active wear-facing) layer may comprise a fibre derived from a synthetic material, such as nylon or polymer such as polyamide elastane.

The operatively outer layer may be treated with a water-repelling substance. The water repelling substance may include perfluoroctanesulfonamide or a hydrocarbon polymer. The water repelling substance may be a commercially available substance such as, for example, 3M Scotchgard® or Aquapel® by Nano-Tex®. The water-repelling treatment may be provided on each ace of the fabric of the outer layer, i.e. back and front.

The operatively outer fabric may have a thickness of between 0.1 mm and 2 mm, preferably between 0.2 mm and 1 mm, most preferably no more than 2.0 mm.

The operatively outer fabric may have a weight in a range of 100 gsm to 300 gsm, preferably between 250 and 300 gsm, most preferably 270 gsm.

The total thickness of the protective insert may be between 2 mm and 10 mm, preferably having a maximum thickness of no more than 5 mm, most preferably having a maximum thickness of no more than 3 mm.

The protective insert may be used within, fused to, associated with, or attached to a swimwear garment, typically swimwear tops and swimwear bottoms, to active-wear, typically gym tights or running shorts and dancewear, typically leggings or leotard. Similarly, the protective insert may be used within, fused to, associated with, or attached to only a bra section of a swimwear garment e.g. if required for breastfeeding mothers to prevent breastmilk leaks.

The garment may be in the form of a bikini, one piece, rashie, sports bra, maternity swimwear, maternity sports bra, leotard, gym tights, running shorts and the like.

The protective insert may be fixed or attached to the active, dance or swimwear garment in, proximal to, substantially covering, or extending over, at least part of a bodily discharge zone, such as, for example, in the groin area of gym tights, swimwear bottoms or leotard.

The protective insert outer operatively layer may form the outside layer of the garment.

The article of clothing may be an active, dance or swimwear garment. As such, the invention extends to an article of swimwear having associated therewith the protective insert of the invention.

As such, the invention extends to an article of active wear having associated therewith the protective insert of the invention.

As such, the invention extends to an article of dance wear having associated therewith the protective insert of the invention.

The invention further extends to a method of manufacturing a protective active-wear, dancewear or swimwear, the method including the steps of: providing a first, operatively inner layer as described hereinbefore; bringing into close contact with the first, operatively inner layer, an operatively outer fabric of a breathable, water repellent material for preventing leaking, as described hereinbefore.

According to yet another aspect of the invention, there is provided a method of manufacturing an active, dance or swimwear garment having one or more moisture-absorbing zones, the method including the steps of:

providing a protective insert of the invention; and attaching the protective insert to an area of a garment such that the positioning of the protective insert corresponds to a moisture leakage producing area of a wearer's body.

BRIEF DESCRIPTION OF THE DRAWINGS

The description will be made with reference to the accompanying drawings in which.

DESCRIPTION OF EMBODIMENTS

Figure 1:
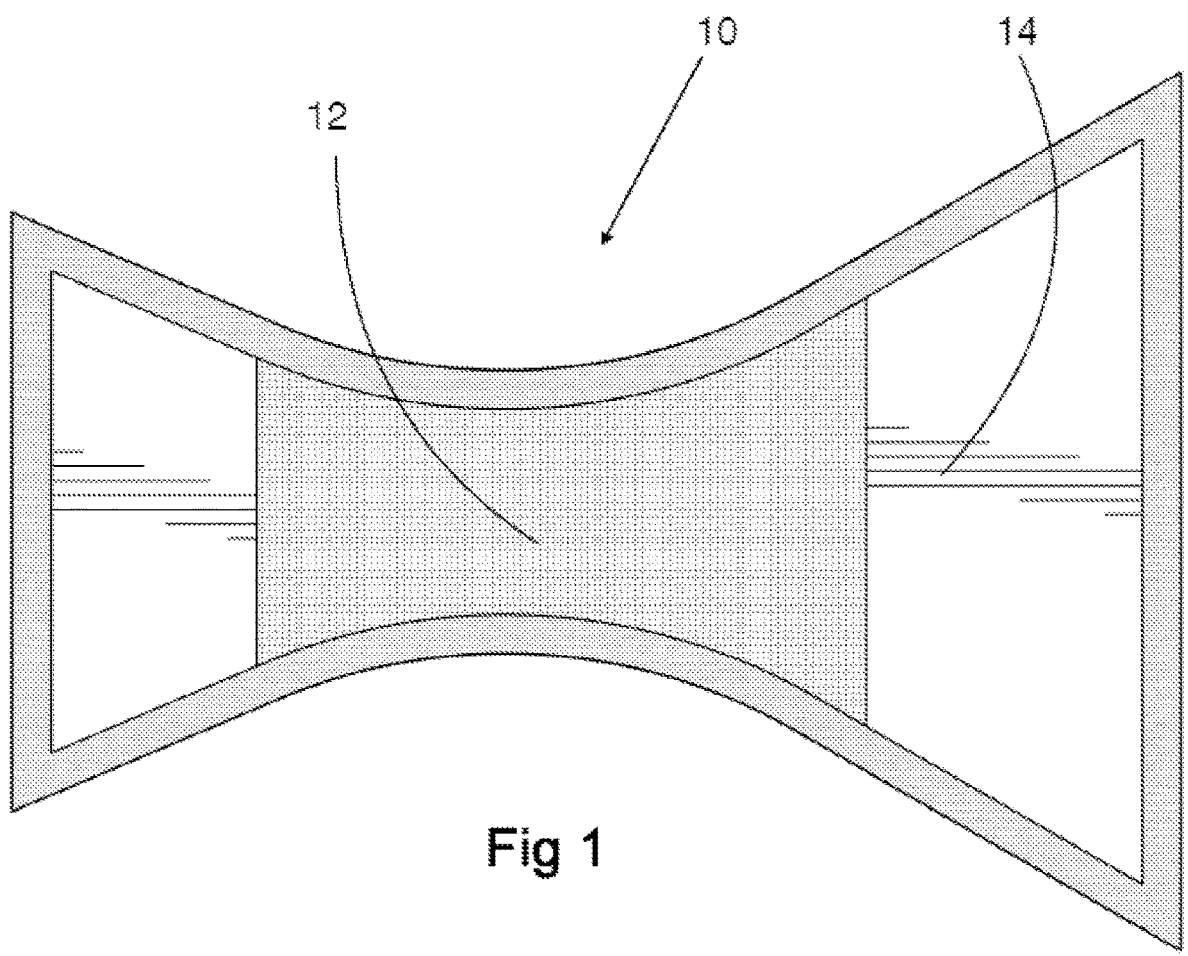
FIG. 1 is a top plan view of an inner groin area of a protective swimwear or dance leotard in accordance with one aspect of the invention, showing the two layers of an insert in accordance with one aspect of the invention.

Further features of the present invention are more fully described in the following description of several non-limiting embodiments thereof. This description is included solely for the purposes of exemplifying the present invention to the skilled addressee. It should not be understood as a restriction on the broad summary, disclosure or description of the invention as set out above. In the figures, incorporated to illustrate features of the example embodiment or embodiments, like reference numerals are used to identify like parts throughout.

Figure 2A:
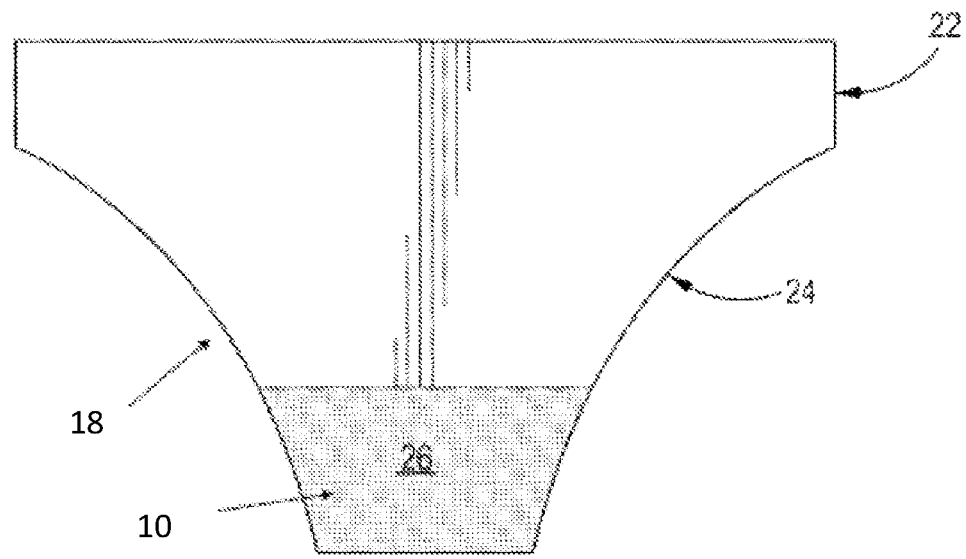
FIG. 2A is a front view of a swimwear bikini bottom in accordance with one aspect of the invention.

With reference now to the accompanying drawings, the invention provides for a quick drying, antibacterial, odour absorbing, breathable and protective insert 10 comprising a first, operatively (in use) inner layer 12, and an operatively (in use) outer layer 14, shown in the context of an article of active, dance or swimwear 18, best shown as a lower section of a bikini as represented in FIG. 2A.

However, the skilled addressee will appreciate that the insert 10 can be used with a wide variety of garments, depending on requirements. As such, the insert 10 may be used with active wear, dancewear, swimwear and/or any other types of garments where such protective insert may find an application.

The protective insert 10 is a slim (3 mm in thickness or less), wicking, moisture spreading, quick drying, antibacterial, breathable, comfortable water repellent insert, which can prevent leakages of up to 5-10 ml in a single insult. The swimwear 18 (including insert 10) is machine washable, obviating the need for hand washing, while being durable and capable of lasting as long as regular swimwear.

The protective insert 10 and resultant swimwear 18 provide a comfortable and sustainable way to stay dry and fresh from light bladder leaks, menstrual overflow/spotting, discharge, and breastmilk leaks without the need for disposable liners, allowing women (and men susceptible to bladder leakage) to participate in swimming, dancing and exercise without fear.

The inner (first) layer 12 comprises a slim synthetic material, commercially available under the brand name "Coolmax" or "Coolmesh", which comprises polyester wicking fibres. Coolmax fibres are not round, but are slightly oblong in cross-section with grooves running lengthwise along the threads. They are manufactured in either a tetra-channel or hexachannel style. The series of closely spaced channels creates capillary action that wicks moisture through the core and out to a wider area on the surface of the fabric which increases evaporation.

The Applicant has found much experimentation that a polyester wicking fibre like Coolmax or Coolmesh fabric has rapid moisture wicking (hydrophilic) and fast drying capabilities. Applicant has also found that that the polyester wicking fabric is highly absorbent, given that the fabric allows the moisture to rapidly spread over the entire surface, the fabric typically being capable of absorbing and retaining up to 10 ml for every 10 cm×10 cm area of the fabric of the inner layer 12. The absorption is further improved with a water laminate film on the bottom of the fabric.

The polyester fabric forming part of the inner layer 12, is in the form of a mesh fabric. Applicant has found the mesh structure aids rapid drying, as the structure allows air to flow through the fabric and insert 10, thereby assisting in the drying process.

Applicant has also found that the polyester fabric either combined with bamboo-charcoal fibres or impregnated or coated with odour absorbing compositions or treatment acts to absorb and eliminate unwanted odour caused by ammonia and body odour.

The polyester fabric, in certain embodiments, may be further impregnated or coated with antimicrobial treatments, usually silver ion-based products, like Silpure® or Ultra-Fresh®, or other commercially available antimicrobial compounds or compositions, or mixtures thereof, to further enhance the antimicrobial and/or odour eliminating capabilities of the polyester fabric.

The polyester fabric, in certain embodiments, can also be fused to a waterproof laminate-film to support the absorbency and to give additional leak-proof capacity.

In the embodiment shown in FIG. 1, the operatively outer fabric 14 comprises a nylon or polyester fabric generally having a thickness of 1 mm or less, commercially available, in this embodiment, as polyamide elastane. The fabric has a water repellent hydrocarbon polymer treatment, typically Aquapel® by Nano Tex®, on the front and back surfaces making it moisture repellent, thereby acting as a further barrier against leaks and, increasing the drying time by double in comparison to regular untreated active, dance or swimwear fabric after full submersion in water. However, this layer does allow for air penetration, which assists with drying the inner layer and ameliorating microbial growth.

The first, inner, layer is sewn and/or fused onto the outer fabric as shown in FIG. 1.

Figure 2B:
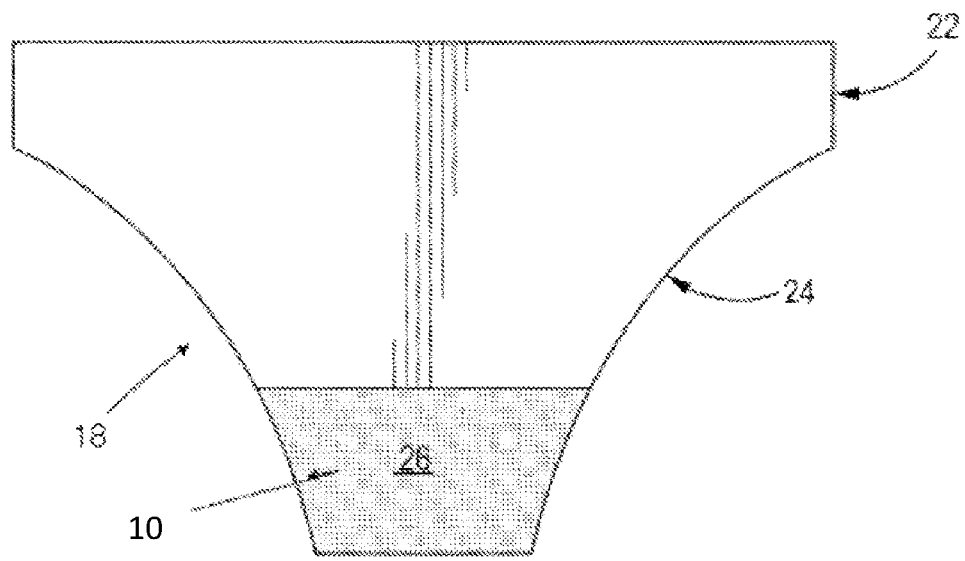
FIG. 2B is a rear view of swimwear bikini bottom in accordance with one aspect of the invention.

Turning now to FIGS. 2A and 2B, there is shown a pair of bikini bottoms that include a body 22, cut-outs for legs 24, and a general crotch area 26. The protective first layer of the insert 10 of the invention is sewn or fused to the outer fabric of the general crotch area 26 and extends sufficiently to cover crotch areas prone to accidental fluid leakage that may be experienced by a wearer.

Figure 3A:
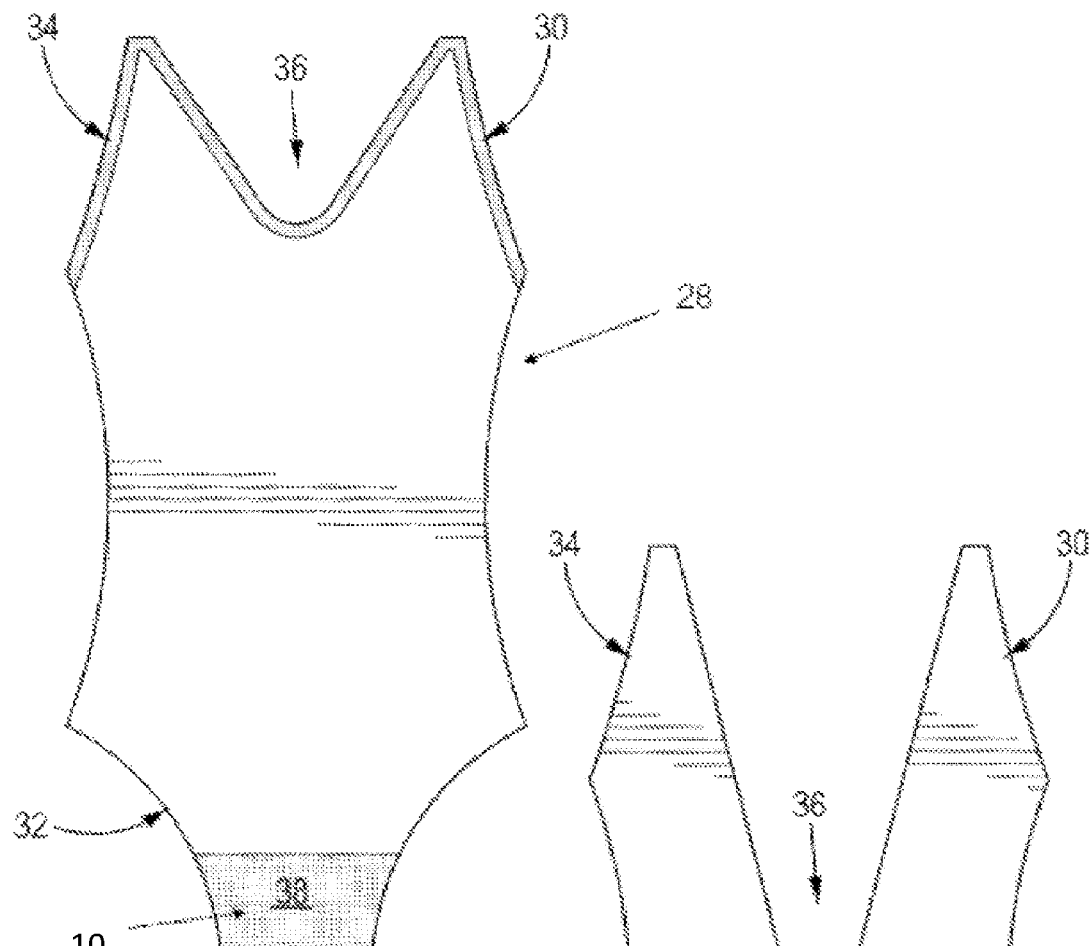
FIG. 3A is a rear view of swimwear full piece or dance leotard in accordance with one aspect of the invention.
Figure 3B:
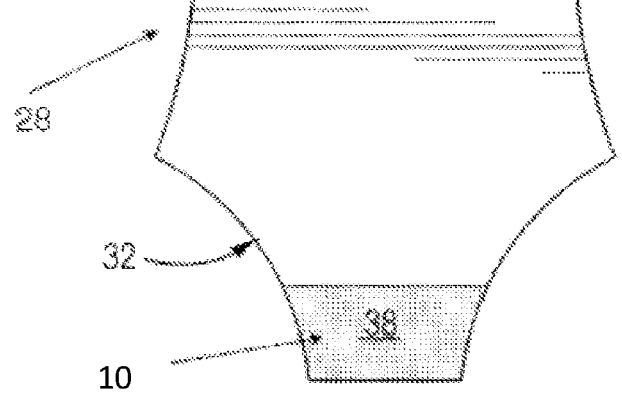
FIG. 3B is a front view of a swimwear full piece or dance leotard in accordance with one aspect of the invention.

Turning now to FIG. 3, there is provided a full-piece swimwear or dance leotard garment 28. The garment includes a body 30, cut-outs 32 for wearer's legs, cut-outs 34 for a wearer's arms (not shown) and a cut-out 36 for a wearer's neck. The protective first layer is sewn or fused to the outer fabric of the general crotch area 38 and extends sufficiently to cover crotch areas prone to accidental fluid leakage that may be experienced by a wearer.

Figure 4:
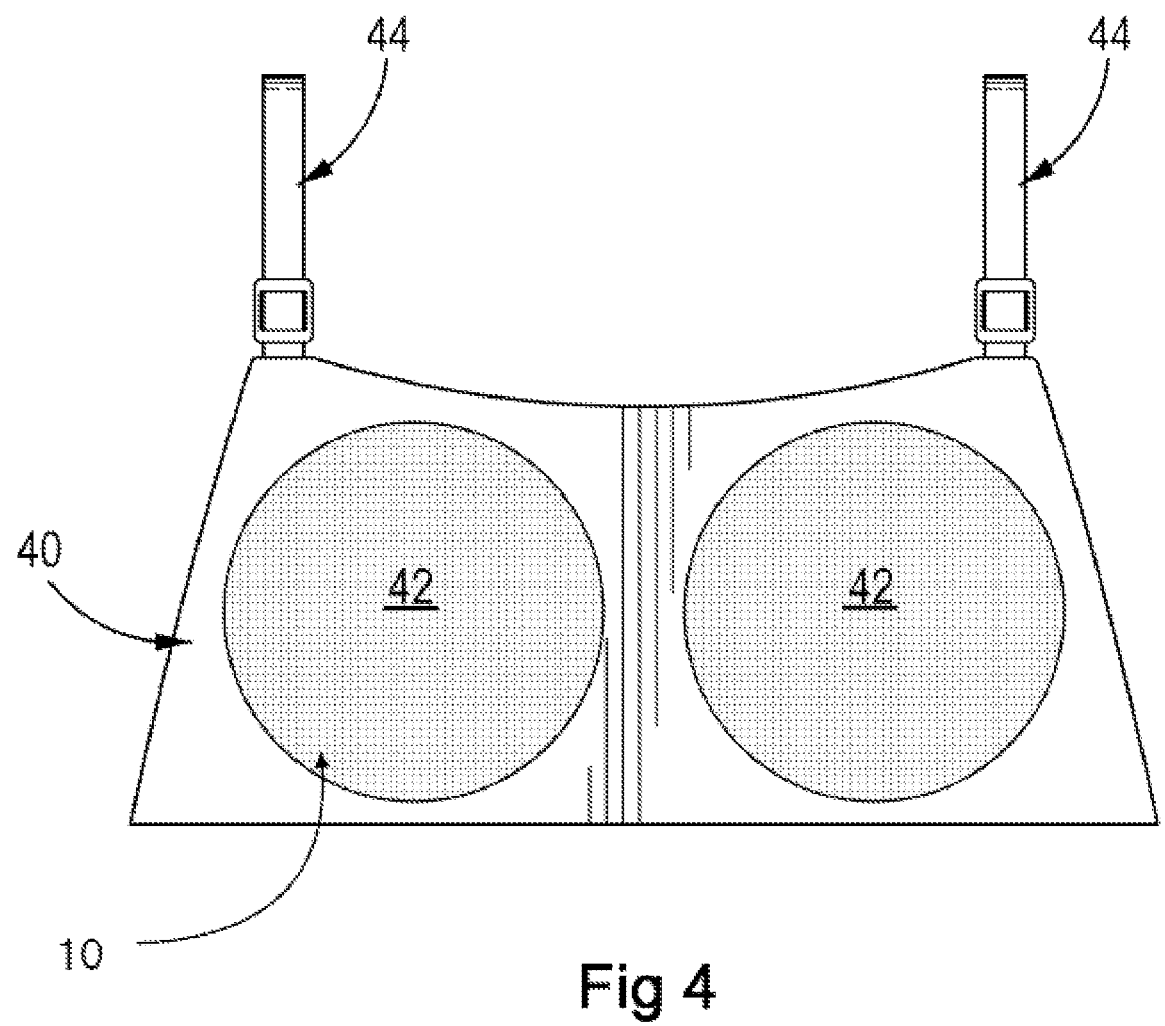
FIG. 4 is a front view of a swimwear maternity top, in accordance with one aspect of the invention.

Turning now to FIG. 4, there is provided a swimwear maternity top 40 for lactating women. The swimwear maternity top 40 includes a body 42, generally comprising two cups 44, and connecting straps 46. The protective first layer 12 of the insert 10 is sewn or fused to the inside of each cup 44 (and may in certain embodiments replace the cups 44 themselves in their entirety) and extends sufficiently to cover all areas prone to accidental fluid leakage experienced by a wearer.

The skilled addressee will appreciate that the insert 10 is applicable to any type of garment or article of clothing, depending on user requirements. As such, the insert of the present invention extends to any suitable garment, including all dance, active and swimwear, such as leggings, upper body garments, etc.

The Applicant is of the opinion that they have developed a protective insert and a line of active, dance and swimwear that can be worn during a woman's menstrual cycle or for pelvic floor support that protects against light bladder leakage or period flow (up to 10 ml). To this end, several experiments were conducted over a period of 4 months, as described below.

Experiment 1

A polyamide elastane with 3M Scotchgard-treated fabric was soaked in pool water for 30 minutes and then washed by hand with a dab of laundry detergent and then dried. After drying, 10 ml of liquid was poured onto the garment to test that the fabric is still waterproof for longer than 15 minutes
Water Repellent Durability
Under 30 washes—Fail
Over 50 washes—Pass
Drying Speed
Slow=2 hrs or more
Moderate=1-2 hrs
High=30 minutes-1 hr
Very High=Less than 30 minutes

| Day | 10 ml water | Drying Speed |
| --- | --- | --- |
| 1 | Passed 2 tests | Very high |
| 2 | Passed 2 tests | Very high |
| 3 | Passed 1 test | Very high |
| 4 | Passed 2 tests | Very high |
| 5 | Passed 1 test | Very high |
| 6 | Passed 3 tests | Very high |
| 7 | Passed 2 tests | Very high |
| 8 | Passed 3 tests | High |
| 9 | Passed 1 test | High |
| 10 | Passed 2 tests | High |
| 11 | Passed 2 tests | High |
| 12 | Passed 2 tests | High |
| 13 | Passed 1 test, Failed 2 tests | High |
| 14 | Failed 1 test | High |
| 15 | Failed 2 tests | High |
| 16 | Failed 2 tests | High |

Experiment 2

A polyamide elastic Aquapel by Nano-Tex fabric was soaked in pool water for 30 minutes and then washed by hand with a dab of laundry detergent and then dried. After drying, 10 ml of liquid is poured onto the garment to test that the fabric is still waterproof for longer than 15 minutes.
Water Repellent Durability
Under 30 washes—Fail
Over 50 washes—Pass
Drying Speed
Slow=2 hrs or more
Moderate=1-2 hrs
High=30 minutes-1 hr
Very High=Less than 30 minutes

| Day | 10 ml water | Drying Speed |
| --- | --- | --- |
| 1 | Passed 3 tests | Very high |

-continued

| Day | 10 ml water | Drying Speed |
| --- | --- | --- |
| 2 | Passed 3 tests | Very high |
| 3 | Passed 3 test | Very high |
| 4 | Passed 2 tests | Very high |
| 5 | Passed 1 test | Very high |
| 6 | Passed 2 tests | Very high |
| 7 | Passed 2 tests | Very high |
| 8 | Passed 3 tests | Very high |
| 9 | Passed 3 test | Very high |
| 10 | Passed 3 tests | Very high |
| 11 | Passed 3 tests | Very high |
| 12 | Passed 4 tests | Very high |
| 13 | Passed 4 tests | Very high |
| 14 | Passed 2 tests | Very high |
| 15 | Passed 1 test | Very high |
| 16 | Passed 3 test | Very high |
| 17 | Passed 4 test | Very high |
| 18 | Passed 1 test | Very high |
| 19 | Passed 1 test | Very high |
| 20 | Passed 3 test | Very high |
| 21 | Passed 3 test | Very high |

Experiment 3

From the above experiments it was found that a synthetic nylon or polyester fabric, treated with commercially available water repellent under the trade name Aquapel produced by Nano-Tex, was superior. This fabric was combined with a number of moisture-wicking fabrics to determine a fabric that offers superior moisture wicking properties (so that it feels dry following leakage), can hold the most fluid, and is most quick drying and dry to the skin.
    Wicking polyester mesh
    Moisture wicking nylon spandex
    Carbon-Polyester spandex

| | Speed of wicking | Dryness level | Absorption | Speed of drying when worn in sun |
| --- | --- | --- | --- | --- |
| Wicking polyester mesh | 1 s | Could hold 7 ml and still feel semi-dry to touch | 20 ml | 28 minutes |
| Wicking polyester mesh | 1 s | Could hold 7 ml and still feel semi-dry to touch | 15 ml | 25 minutes |
| Wicking polyester mesh | 1 s | Could hold 5 ml and still feel semi-dry to touch | 20 ml | 29 minutes |
| Moisture wicking nylon spandex | 3 s | Could hold 2.5 ml and still feel semi-dry to | 5 ml | 26 minutes |
| Moisture wicking nylon spandex | 2 s | Could hold 2.5 ml and still feel semi-dry to | 7 ml | 22 minutes |
| Moisture wicking nylon spandex | 3-4 s | Could hold 3.5 ml and still feel semi-dry to | 10 ml | 25 minutes |
| Carbon-Polyester spandex | 1 s | Saturation | Low, water pools | 15 minutes |
| Carbon-Polyester spandex | 1 s | Saturation | Low, water pools | 17 minutes |
| Carbon-Polyester spandex | 2 s | Saturation | Low, water pools and leaked off the edge | 20 minutes |

Experiment 4

A synthetic Aquapel fabric was made into swimwear with a gusset layer of wicking polyester mesh fabric without waterproof laminate. The garment was soaked in pool water for 30 minutes and then washed by hand with a dab of laundry detergent and then dried. After drying, 10 ml of liquid was poured onto the garment to test that the fabric can hold the liquid without leaking through the bottom and to test how long the garment takes to dry. 50 tests were performed to ensure durability of garment.

Water Repellent to Hold 10 ml

Fail

Pass

Drying Speed

Slow=2 hrs or more

Moderate=1-2 hrs

High=30 minutes-1 hr

Very High=Less than 30 minutes

| Day | 10 ml water | Drying Speed |
| --- | --- | --- |
| 1 | Passed 3 tests | Very high, very high, Very high |
| 2 | Passed 3 tests | Very high, very high, Very high |
| 3 | Passed 3 test | Very high, very high, Very High |
| 4 | Passed 2 tests | Very high, very high |
| 5 | Passed 1 test | Very high |
| 6 | Passed 2 tests | Very high, Very High |
| 7 | Passed 2 tests | Very high, very high |
| 8 | Passed 3 tests | Very high, Very High, Very high |
| 9 | Passed 3 test | Very high, VH, VH |
| 10 | Passed 3 tests | Very high, VH, VH |
| 11 | Passed 3 tests | Very high, very High, Very high |
| 12 | Passed 4 tests | Very high, very high, very high |
| 13 | Passed 4 tests | Very high, very high, very high |
| 14 | Passed 2 tests | Very high, very high |
| 15 | Passed 1 test | Very high |
| 16 | Passed 3 test | Very high, Very high |
| 17 | Passed 4 test | Very high, Very high, Very high |
| 18 | Passed 1 test | Very high |
| 19 | Passed 1 test | Very high |
| 20 | Passed 3 test | Very high, Very high, Very high |
| 21 | Passed 3 test | Very high, Very high, Very high |

Experiment 5

Because Nano-Tex is only water repellent when not fully submerged in water to further leak proof a swimwear garment when it was wet it was decided a layer of waterproof laminate was required. A synthetic Aquapel fabric was made into swimwear with a gusset layer of wicking polyester mesh fabric with waterproof laminate. The garment was soaked in pool water for 30 minutes and then 10 ml of liquid was poured onto the garment to test that the fabric can hold the liquid without leaking through the bottom. 50 tests were performed to ensure durability of garment.

Water Repellent to Hold 10 ml
Fail
Pass
Drying Speed
Slow=2 hrs or more
Moderate=1-2 hrs
High=30 minutes-1 hr
Very High=Less than 30 minutes

| Day | 10 ml water | Drying Speed |
|---|---|---|
| 1 | Passed 1 tests | Very high |
| 2 | Passed 1 tests | Very high |
| 3 | Passed 1 tests | Very high |
| 4 | Passed 2 tests | Very high, very high |
| 5 | Passed 1 test | Very high |
| 6 | Passed 1 test | Very high |
| 7 | Passed 1 test | Very high |
| 8 | Passed 5 tests | Very High × 5 |
| 9 | Passed 1 test | Very high |
| 10 | Passed 1 test | Very high |
| 11 | Passed 3 tests | Very high, very High, Very high |
| 12 | Passed 5 tests | Very high, very high, very high, Very High |
| 13 | Passed 5 tests | Very high, very high, very high, Very High |
| 14 | Passed 2 tests | Very high, very high |
| 15 | Passed 2 tests | Very high, very high |
| 16 | Passed 1 test | Very high |
| 17 | Passed 1 test | Very high |
| 18 | Passed 1 test | Very high |
| 19 | Passed 1 test | Very high |
| 20 | Passed 1 test | Very high |
| 21 | Passed 1 test | Very high |
| 22 | Passed 1 test | Very high |
| 23 | Passed 1 test | Very high |
| 23 | Passed 4 test | Very high, very high, very high, very high |
| 23 | Passed 2 test | Very high, very high |
| 23 | Passed 4 test | Very high, very high, very high, very high |

The Applicant is of the opinion that they have invented an environmentally friendly, reusable, launderable, moisture and odour controlling, fashionable, comfortable active, dance or swimwear which is unobtrusive and discreet yet can absorb and prevent up to 10 ml of bodily fluids leaking through in the crotch or upper body area and which prevents penetration of moisture to the exterior of the garment. Advantageously, the combination of layers in accordance with the protective active, dance or swimwear results in a garment that is even quicker drying than regular active, dance and swimwear thus could be worn by any person seeking more comfort and more dryness in their active, dance and swimwear.

Optional embodiments of the present invention may also be said to broadly consist in the parts, elements and features referred to or indicated herein, individually or collectively, in any or all combinations of two or more of the parts, elements or features, and wherein specific integers are mentioned herein which have known equivalents in the art to which the invention relates, such known equivalents are deemed to be incorporated herein as if individually set forth. In the example embodiments, well-known processes, well-known device structures, and well-known technologies are not described in detail, as such will be readily understood by the skilled addressee.

The use of the terms "a", "an", "said", "the", and/or similar referents in the context of describing various embodiments (especially in the context of the claimed subject matter) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. As used herein, the term "and/or" includes any and all combinations of one or more of the associated listed items. No language in the specification should be construed as indicating any non-claimed subject matter as essential to the practice of the claimed subject matter.

It is to be appreciated that reference to "one example" or "an example" of the invention, or similar exemplary language (e.g., "such as") herein, is not made in an exclusive sense. Various substantially and specifically practical and useful exemplary embodiments of the claimed subject matter are described herein, textually and/or graphically, for carrying out the claimed subject matter.

Accordingly, one example may exemplify certain aspects of the invention, whilst other aspects are exemplified in a different example. These examples are intended to assist the skilled person in performing the invention and are not intended to limit the overall scope of the invention in any way unless the context clearly indicates otherwise. Variations (e.g. modifications and/or enhancements) of one or more embodiments described herein might become apparent to those of ordinary skill in the art upon reading this application. The inventor(s) expects skilled artisans to employ such variations as appropriate, and the inventor(s) intends for the claimed subject matter to be practiced other than as specifically described herein.

Any method steps, processes, and operations described herein are not to be construed as necessarily requiring their performance in the particular order discussed or illustrated, unless specifically identified as an order of performance. It is also to be understood that additional or alternative steps may be employed.

The invention claimed is:

1. A garment that absorbs up to 10 mls of body fluid in a single insult from a moisture leakage producing area of a wearer's body through to an exterior of the garment, the garment consisting of:
   a body-facing inner fabric layer configured to be disposed adjacent the moisture leakage producing area of a wearer's body and comprising a moisture-wicking, fluid absorbent natural fibre, a moisture-wicking, fluid absorbent fibre derived from a natural fibre, or a moisture-wicking, fluid absorbent synthetic fibre, or a combination of moisture-wicking, fluid absorbent natural and synthetic fibres in the form of a woven or knitted fabric having a thickness of less than about 2 mm and a fibre weight of between 100 gsm and 300 gsm, with or without a breathable fluid resistant laminate-film interposed between the inner fabric layer and an outer layer of the garment;

wherein the outer layer of the garment comprises breathable, water repellent fibres of nylon or a polymer of polyester or polyamide elastane with a fibre weight of between 100 gsm to 300 gsm, the outer layer comprising a water repelling substance and having a thickness of less than about 2 mm; and wherein the garment dries from saturation in less than about 30 minutes.

2. The garment of claim 1, wherein the garment is a swimwear garment, an active wear garment, or a dance wear garment.

3. The garment of claim 1, wherein the fabric of the outer layer or each face of the fabric of the outer layer is treated with a water-repelling substance to prevent fluid passage through the garment.

4. The garment of claim 1, wherein the water repellent fibre of the fabric of the outer layer is treated with a water repellent hydrocarbon polymer treatment.

5. The garment of claim 3, wherein the water-repelling substance comprises perfluoroctanesulfonamide or a hydrocarbon polymer.

6. The garment of claim 1, wherein the fluid resistant laminate film is interposed between the inner and the outer layer.

7. The garment of claim 1, wherein the inner layer fabric is configured to be hydrophilic and/or contains a hydrophilic compound.

8. The garment of claim 1, wherein the inner layer fabric is selected to allow for the spreading and drying of 5-10 ml of moisture or bodily secretions in less than 5 to 10 minutes for drying each mL of moisture of bodily secretions per 10 cm×10 cm.

9. The garment of claim 1, wherein the inner layer fabric is pre-treated to enhance the moisture-absorbing or moisture-wicking capabilities thereof.

10. The garment of claim 1, wherein the inner layer fabric is in the form of natural fabric or a synthetic fabric selected from polyester or nylon.

11. The garment of claim 1, wherein the outer fabric comprises nylon, or a polyester or polyamide elastane polymer.

12. The garment of claim 1, wherein the inner layer is in the form of a nylon or polyester woven or knitted mesh fabric.

13. The garment of claim 1 which is a swimwear garment, wherein:
the inner layer comprises a moisture-wicking, fluid absorbent nylon or polyester fibre in the form of a woven or knitted fabric;
the outer layer comprises a water repellent nylon or polyamide elastane fabric, wherein the outer layer of the insert forms an outside layer of the garment;
wherein a waterproof laminate-film is interposed between the inner and the outer layer; and
wherein the outer layer is treated with a water-repelling substance to prevent fluid passage through the swimwear garment.

14. The garment of claim 1 which is an active wear or dance wear garment, wherein:
the inner layer comprises a moisture-wicking, fluid absorbent nylon or a moisture-wicking, fluid absorbent polyester fibre in the form of a woven or knitted fabric; and
the outer layer comprises a nylon or a polyamide elastane fabric, wherein the outer layer is treated with a water repelling substance to prevent fluid passage through the garment.

15. The garment of claim 14, wherein the outer layer of the insert forms an outside layer of the active wear or dance wear garment.

16. The garment of claim 13, wherein the outer layer of the insert forms an outside layer of the swim wear garment.

17. The garment of claim 1, wherein the moisture leakage producing area of a wearer's body is a crotch region.

18. The garment of claim 1, wherein the garment is machine launderable.

19. The garment of claim 1, wherein the moisture-wicking, fluid absorbent woven or knitted fabric comprises a polyester.

20. The garment of claim 1, wherein the woven or knitted fabric is a mesh.

21. The garment of claim 1, wherein the water repelling substance comprises a hydrocarbon polymer.

22. The garment of claim 1, in the form of a swimwear garment, wherein:
the inner layer is associated with a breathable waterproof laminate-film on an outer part of the inner layer for additional waterproof effect; and
the outer layer comprises nylon or polyamide elastane, whereby the outer layer or each face of the outer layer is treated with the water repelling substance to prevent fluid passage through the garment.

23. The garment of claim 22, wherein:
the inner layer is a wicking knitted polyester fabric with a waterproof laminate to prevent fluid passage through the garment; and
the outer layer or each face of the outer layer is treated with a synthetic hydrocarbon polymer treatment and is extended to form a body of the swimwear garment.

24. The garment of claim 22, wherein the outer layer has a thickness of about 1 mm or less, and the synthetic hydrocarbon polymer treatment is applied to front and back surfaces of the outer layer making it moisture repellent but air penetrable.

25. A garment in the form of an active wear, a dance wear or a swim wear garment that absorbs up to 10 mls of body fluid received in a single insult from a crotch area of the garment through to the garment exterior, the garment comprising:
a body-facing inner layer in the crotch area comprising a moisture-wicking, fluid absorbent woven or knitted fabric comprising nylon or polyester having a thickness of less than about 2 mm and a fibre weight of between 100 gsm and 300 gsm, with or without a breathable fluid resistant laminate-film interposed between the inner layer and an outer layer of the garment; and
wherein the outer layer of the garment comprises breathable, water repellent fibres of nylon or a polymer of polyester or polyamide elastane with a fibre weight of between 100 gsm to 300 gsm, the outer layer or each face of the outer layer treated with a water-repelling substance to prevent fluid passage through the garment and has a thickness of less than about 2 mm, wherein the garment dries from saturation in less than about 30 minutes.

26. A garment in the form of a swim wear garment that absorbs up to 10 mls of body fluid received in a single insult from a crotch area of the garment through to the garment exterior, the garment comprising:

a body facing inner layer in the crotch area comprising a moisture-wicking, fluid absorbent woven or knitted fabric comprising nylon or polyester having a thickness of less than about 2 mm and a fibre weight of between 100 gsm and 300 gsm, with a breathable fluid resistant laminate-film interposed between the inner layer and an outer layer of the garment; and wherein the outer layer of the garment comprising breathable, water repellent fibres of nylon or a polymer of polyester or polyamide elastane with a fibre weight of between 100 gsm to 300 gsm, the outer layer or each face of the outer layer treated with a water-repelling substance to prevent fluid passage through the garment and has a thickness of less than about 2 mm, wherein the garment dries from saturation in less than about 30 minutes.

* * * * *